US012605566B2

(12) United States Patent     (10) Patent No.:   US 12,605,566 B2

Hirai et al.            (45) Date of Patent:     Apr. 21, 2026

(54) MEDICAL IMAGE PROCESSING DEVICE, MEDICAL IMAGE PROCESSING METHOD, MEDICAL IMAGE PROCESSING PROGRAM, AND RADIATION THERAPY DEVICE

(71) Applicants: Toshiba Energy Systems & Solutions Corporation, Kawasaki (JP); National Institutes for Quantum Science and Technology, Chiba (JP)

(72) Inventors: Ryusuke Hirai, Tokyo (JP); Yukinobu Sakata, Kawasaki (JP); Akiyuki Tanizawa, Kawasaki (JP); Keiko Okaya, Tokyo (JP); Shinichiro Mori, Chiba (JP)

(73) Assignees: TOSHIBA ENERGY SYSTEMS & SOLUTIONS CORPORATION, Kawasaki (JP); NATIONAL INSTITUTES FOR QUANTUM SCIENCE AND TECHNOLOGY, Chiba (JP)

( * ) Notice: Subject to any disclaimer, the term of this patent is extended or adjusted under 35 U.S.C. 154(b) by 153 days.

(21) Appl. No.: 18/349,397

(22) Filed: Jul. 10, 2023

(65) Prior Publication Data

US 2023/0347180 A1     Nov. 2, 2023

Related U.S. Application Data

(63) Continuation of application No. PCT/JP2022/007094, filed on Feb. 22, 2022.

(30) Foreign Application Priority Data

Mar. 12, 2021    (JP) .................................. 2021-039812

(51) Int. Cl.
| | |
|---|---|
| *A61N 5/10* | (2006.01) |
| *A61B 90/00* | (2016.01) |
| *G06T 7/246* | (2017.01) |

(52) U.S. Cl.
CPC ............ *A61N 5/1049* (2013.01); *A61B 90/39* (2016.02); *G06T 7/248* (2017.01); (Continued)

(58) Field of Classification Search
CPC .......... A61N 5/1049; A61N 2005/1062; A61N 5/1037; A61N 5/1039; A61N 5/1067; (Continued)

(56) References Cited

U.S. PATENT DOCUMENTS

2008/0009716 A1* 1/2008 Ohishi ...................... G06T 7/73
                                             600/425
2016/0270655 A1* 9/2016 Caraffi ................. A61B 3/0025
(Continued)

FOREIGN PATENT DOCUMENTS

| | | |
|---|---|---|
| JP | 2018-082767 A | 5/2018 |
| JP | 2019-528149 A | 10/2019 |

OTHER PUBLICATIONS

International Search Report and Written Opinion for International Patent Application No. PCT/JP2022/007094 dated Apr. 19, 2022 (12 pages).

*Primary Examiner* — Hien N Nguyen

(74) *Attorney, Agent, or Firm* — Foley & Lardner LLP

(57) ABSTRACT

A medical image processing device includes a first image acquiring unit, a second image acquiring unit, a first likelihood distribution calculating unit, a trackability determining unit, and a tracking unit. The first image acquiring unit acquires first images which are transparent images of the patient. The second image acquiring unit acquires second images which are transparent images of the patient gener- (Continued)

ated at a time different from that of the first images. The first likelihood distribution calculating unit calculates a first likelihood distribution indicating a distribution of likelihoods indicating a likeness to the object in the first images. The trackability determining unit determines whether the object is trackable on the basis of the first likelihood distribution. The tracking unit tracks the position of the object in the second images on the basis of the result of determination.

8 Claims, 8 Drawing Sheets

(52) U.S. Cl.
CPC ................. *A61B 2090/3966* (2016.02); *A61N 2005/1062* (2013.01); *G06T 2207/10116* (2013.01); *G06T 2207/20076* (2013.01); *G06T 2207/30204* (2013.01)

(58) Field of Classification Search
CPC ............ A61N 2005/1061; A61B 90/39; A61B 2090/3966; G06T 7/248; G06T 2207/10116; G06T 2207/20076; G06T 2207/30204; G06T 2207/10121; G06T 7/246
See application file for complete search history.

(56) References Cited

U.S. PATENT DOCUMENTS

| | | | |
|---|---|---|---|
| 2018/0056091 A1 | 3/2018 | Jordan et al. | |
| 2018/0140260 A1 | 5/2018 | Taguchi et al. | |
| 2019/0175136 A1* | 6/2019 | Vogelsang | A61B 6/52 |
| 2019/0388182 A1* | 12/2019 | Kumar | G06T 7/33 |
| 2020/0388041 A1* | 12/2020 | Berlinger | G06T 7/285 |

* cited by examiner

Figure 2:
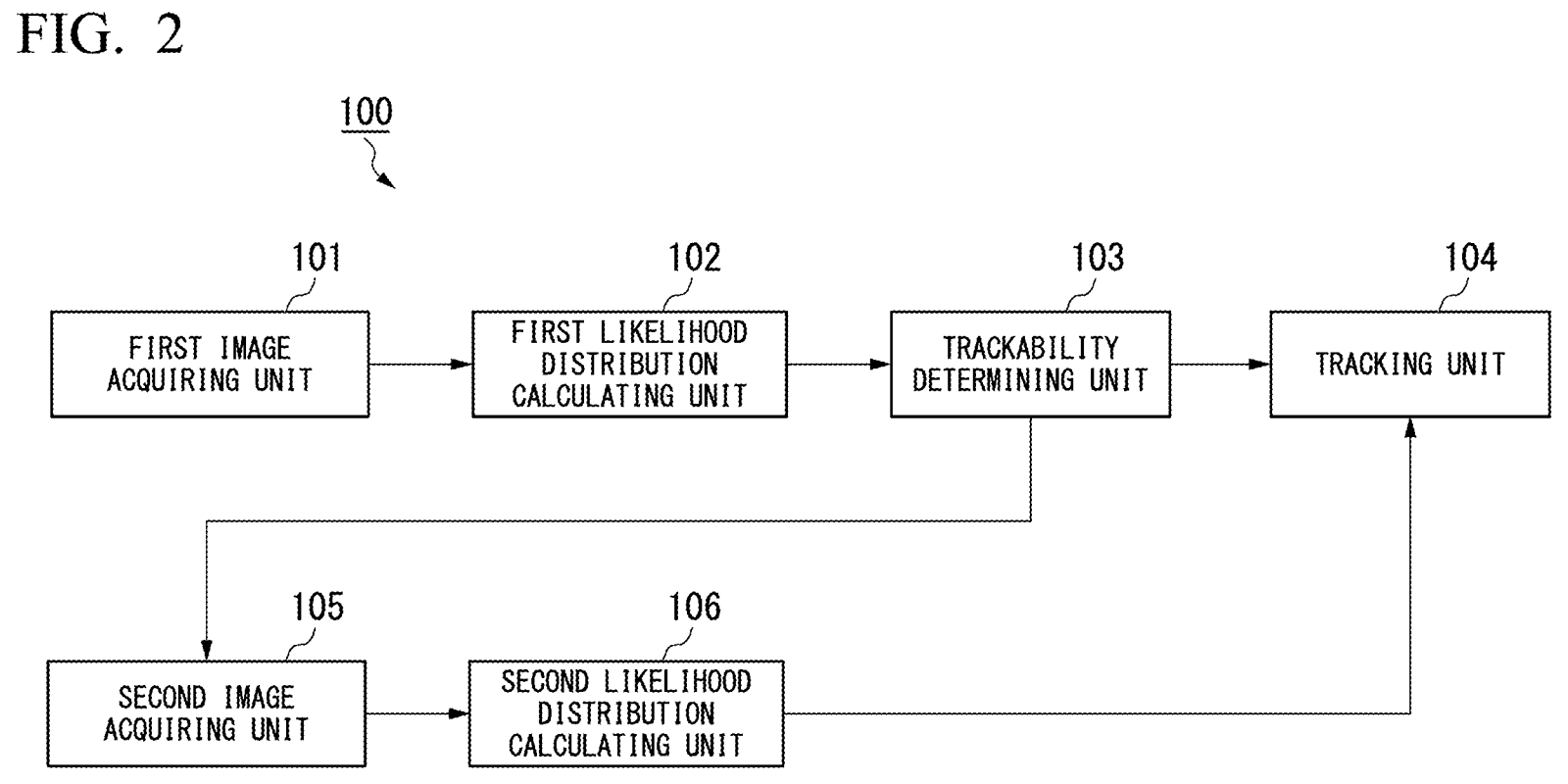

101 — FIRST IMAGE ACQUIRING UNIT

102 — FIRST LIKELIHOOD DISTRIBUTION CALCULATING UNIT

103 — TRACKABILITY DETERMINING UNIT

104 — TRACKING UNIT

105 — SECOND IMAGE ACQUIRING UNIT

106 — SECOND LIKELIHOOD DISTRIBUTION CALCULATING UNIT

START

ACQUIRE FIRST IMAGE — S101

CALCULATE FIRST
LIKELIHOOD DISTRIBUTION — S102

DETERMINE TRACKABILITY — S103

DETERMINE IMAGING
DIRECTION OF SECOND IMAGE — S104

END

START

ACQUIRE SECOND IMAGE — S201

CALCULATE SECOND
LIKELIHOOD DISTRIBUTION — S202

DETERMINE
POSITION OF OBJECT — S203

DETERMINE IRRADIATION
TIMING OF TREATMENT BEAM — S204

END

Figure 7:
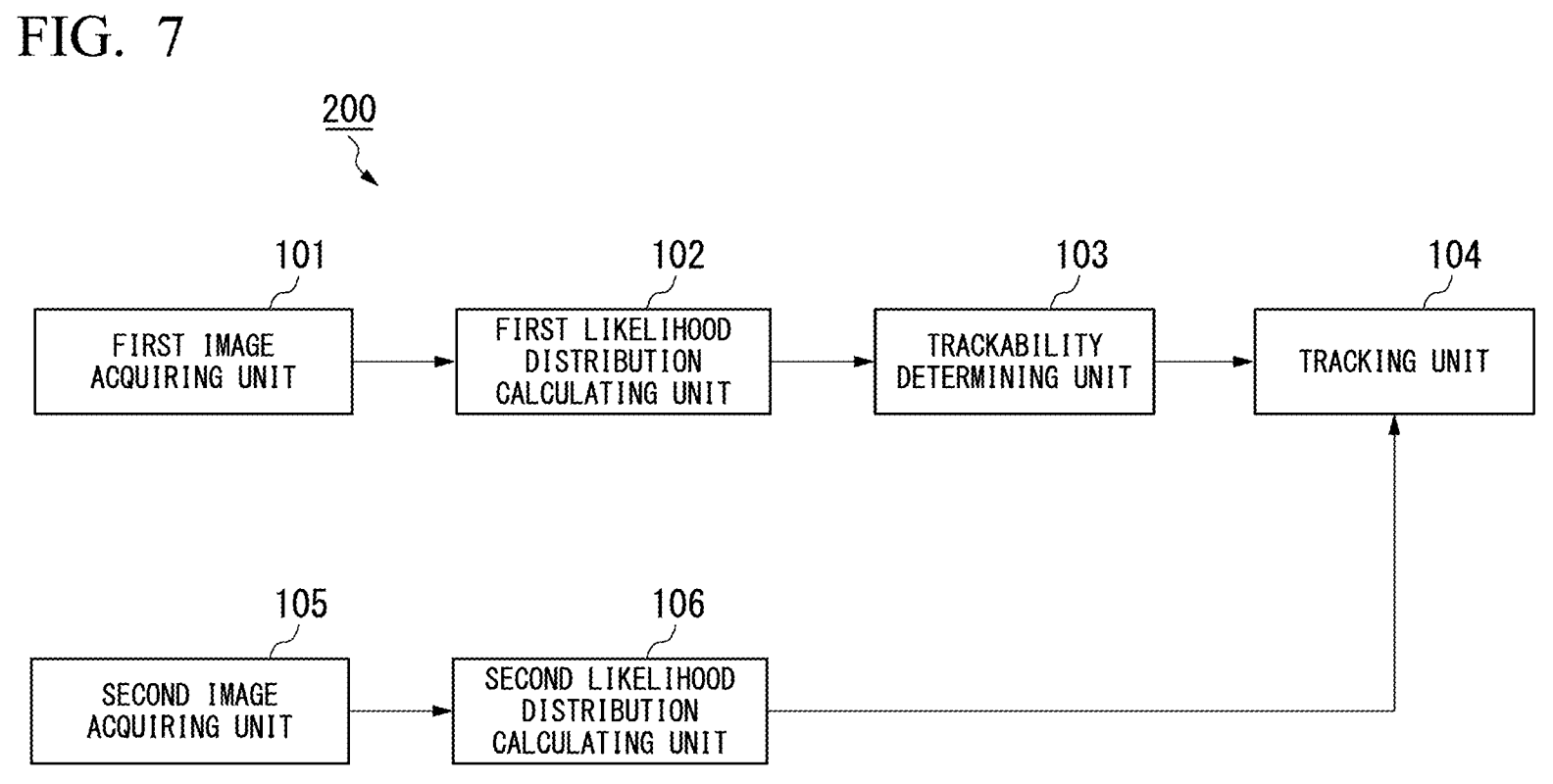

101 FIRST IMAGE ACQUIRING UNIT

102 FIRST LIKELIHOOD DISTRIBUTION CALCULATING UNIT

103 TRACKABILITY DETERMINING UNIT

104 TRACKING UNIT

105 SECOND IMAGE ACQUIRING UNIT

106 SECOND LIKELIHOOD DISTRIBUTION CALCULATING UNIT

MEDICAL IMAGE PROCESSING DEVICE, MEDICAL IMAGE PROCESSING METHOD, MEDICAL IMAGE PROCESSING PROGRAM, AND RADIATION THERAPY DEVICE

CROSS-REFERENCE TO RELATED APPLICATIONS

This application is a continuation of PCT International Application No. PCT/JP2022/007094, filed Feb. 22, 2022, which claims priority to Japanese Patent Application No. 2021-039812, filed Mar. 12, 2021, the disclosures of which are incorporated by reference herein in their entireties.

TECHNICAL FIELD

An embodiment of the present invention relates to a medical image processing device, a medical image processing method, a medical image processing program, and a radiation therapy device.

BACKGROUND ART

Radiation therapy is a treatment method of destroying a lesion in a patient's body by irradiating the lesion with a radiation. Here, a position of a lesion needs to be accurately irradiated with a radiation. This is because normal tissues in a patient's body may be affected when the normal tissues are irradiated with a radiation. Accordingly, when radiation therapy is performed, computed tomography (CT) is first performed in advance in a stage of treatment planning and a position of a lesion in a patient's body is three-dimensionally ascertained. Then, an irradiation direction of a radiation or an irradiation intensity of a radiation is planned such that irradiation of normal tissues is reduced on the basis of the ascertained position of the lesion. Thereafter, in a stage of treatment, a position of the patient is aligned with the position of the patient in the stage of treatment planning, and the lesion is irradiated with a radiation according to the irradiation direction or the irradiation intensity planned in the stage of treatment planning.

In alignment of a patient in the stage of treatment planning, three-dimensional CT data is virtually arranged in a treatment room, and a position of a bed is adjusted such that a position of a patient lying actually on a mobile bed in the treatment room matches the position of the three-dimensional CT data. More specifically, misalignment of the position of the patient between two images including a radiographic image of the patient's body captured in a state in which the patient lies on the bed and a digitally reconstructed radiograph (DRR) obtained by virtually reconstructing a radiographic image from a three-dimensional CT image captured in the stage of treatment planning is calculated by combining the two images. Then, the bed is moved on the basis of the misalignment of the position of the patient calculated through combination of the images to adjust a position of a lesion, a bone, or the like in the patient's body to that in the stage of treatment planning. Thereafter, the lesion is irradiated with a radiation while visually comparing a radiographic image captured again with the DRR image.

When a lesion of the patient is in an organ such as the lungs or the liver which moves due to respiration or heartbeat, the position of the lesion during irradiation needs to be identified. For example, a position of the lesion can be tracked by capturing a radiographic image of the patient who is being irradiated with a radiation. When the lesion does not appear clearly in the radiographic image, the position of the lesion can be indirectly tracked by tracking a marker implanted in the patient's body. The radiation irradiation method includes tracking irradiation of tracking and irradiating a position of a lesion and ambush irradiation of irradiating a lesion when the lesion reaches a position determined in the stage of treatment planning. These irradiation methods are called respiration-synchronized irradiation methods.

However, for example, when an object such as a lesion or a marker overlaps an organ such as the liver with a low X-ray transmittance, the lesion or the marker may not appear clearly in the radiographic image. A pattern such as a rib bone which is not distinguishable well from a marker may be present in the radiographic image. In this case, there is a likelihood that a position of an object such as a lesion or a marker will not be able to be tracked.

CITATION LIST

Patent Literature

[Patent Literature 1]
  Japanese Unexamined Patent Application, First Publication No. 2018-82767

SUMMARY OF INVENTION

Technical Problem

An objective of the present invention is to provide a medical image processing device, a medical image processing method, a medical image processing program, and a radiation therapy device that can track an object in a patient's body with high precision from a transparent image of the patient.

Solution to Problem

A medical image processing device according to an embodiment is a device tracking a position of an object in a patient's body and including a first image acquiring unit, a second image acquiring unit, a first likelihood distribution calculating unit, a trackability determining unit, and a tracking unit. The first image acquiring unit acquires a plurality of first images which are transparent images of the patient and of which imaging directions are different. The second image acquiring unit acquires a plurality of second images which are transparent images of the patient generated at a time different from that of the first images and of which imaging directions are different. The first likelihood distribution calculating unit calculates a first likelihood distribution indicating a distribution of likelihoods indicating a likeness to the object in the plurality of first images acquired by the first image acquiring unit. The trackability determining unit determines whether the object is trackable on the basis of the first likelihood distribution calculated by the first likelihood distribution calculating unit. The tracking unit is configured to track the position of the object in the second images acquired by the second image acquiring unit on the basis of a result of determination from the trackability determining unit.

BRIEF DESCRIPTION OF DRAWINGS

FIG. 2 is a block diagram schematically illustrating a configuration of a medical image processing device according to the first embodiment.

FIG. 7 is a block diagram schematically illustrating a configuration of a medical image processing device according to a second embodiment.

DESCRIPTION OF EMBODIMENTS

Hereinafter, a medical image processing device, a medical image processing method, a medical image processing program, and a radiation therapy device according to an embodiment will be described with reference to the accompanying drawings.

First Embodiment

Figure 1:
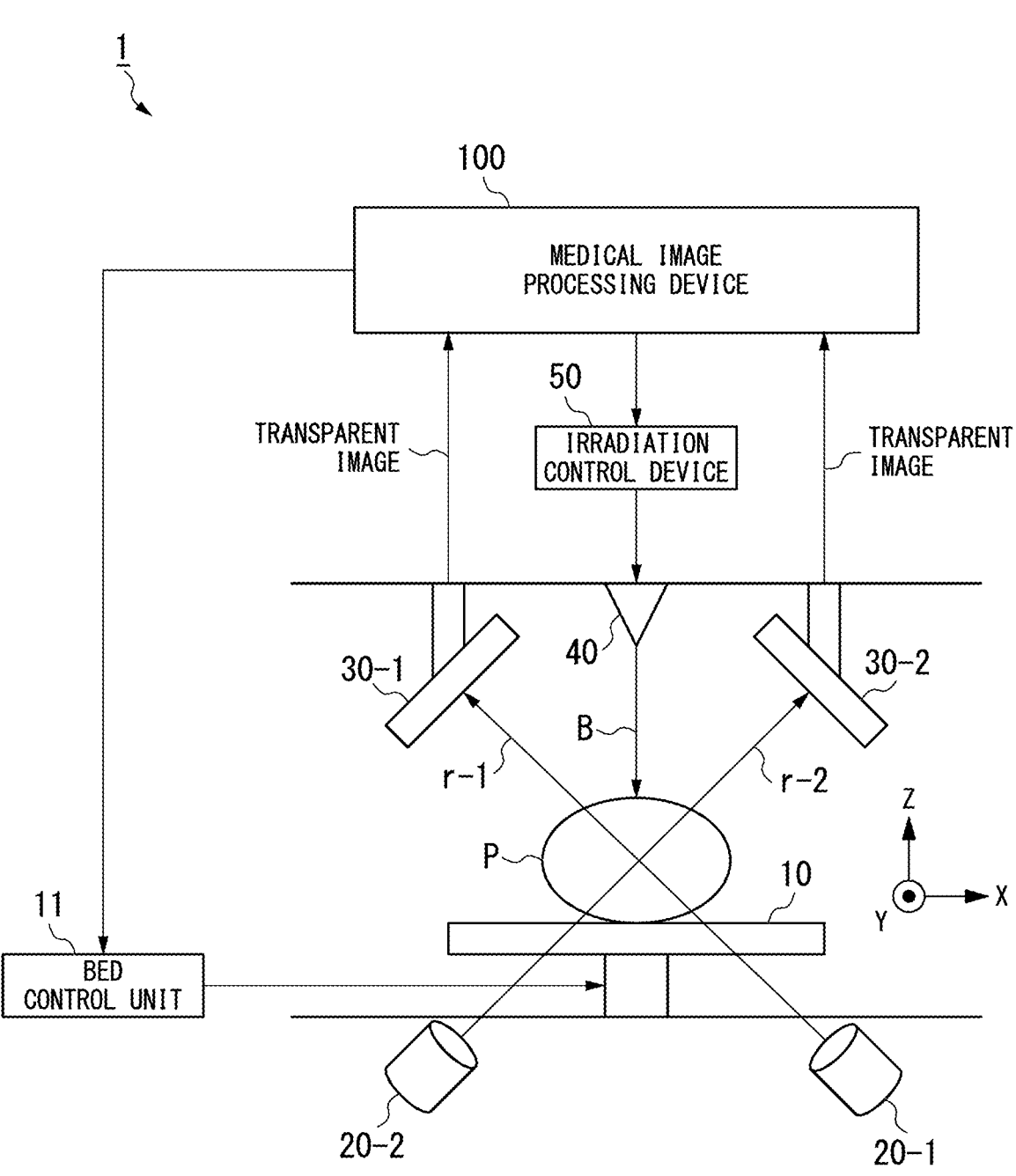
FIG. 1 is a block diagram schematically illustrating a configuration of a treatment system according to a first embodiment.

FIG. 1 is a block diagram schematically illustrating a configuration of a treatment system according to a first embodiment. The treatment system 1 includes, for example, a treatment table 10, a bed control unit 11, two radiation sources 20 (a radiation source 20-1 and a radiation source 20-2), two radiation detectors 30 (a radiation detector 30-1 and a radiation detector 30-2), a treatment beam irradiation door 40, an irradiation control device 50, and a medical image processing device 100.

"-" added to each reference sign and a numeral subsequent thereto in FIG. 1 are for identifying a correspondence relation. More specifically, regarding the correspondence relation between the radiation sources 20 and the radiation detectors 30, the radiation source 20-1 and the radiation detector 30-1 constitute a pair in correspondence, and the radiation source 20-2 and the radiation detector 30-2 constitute a pair in correspondence. When the same two or more elements are not distinguished in the following description, the reference signs are written without using "-" and a numeral subsequent thereto.

The treatment table 10 is a bed on which a sample (patient) P to be subjected to radiation therapy is fixed. The bed control unit 11 is a control unit controlling a translation mechanism and a rotation mechanism provided in the treatment table 10 to change a direction in which a patient P fixed on the treatment table 10 is irradiated with a treatment beam B. For example, the bed control unit 11 controls each of the translation mechanism and the rotation mechanism of the treatment table 10 in three-axis directions, that is, in total six-axis directions.

The radiation source 20-1 irradiates the body of the patient P with a radiation r-1 for seeing through the body from a predetermined angle. The radiation source 20-2 irradiates the body of the patient P with a radiation r-2 for seeing through the body from a predetermined angle different from that of the radiation source 20-1. The radiation r-1 and the radiation r-2 are, for example, X-rays. FIG. 1 illustrates a case in which X-ray imaging is performed on a patient P fixed on the treatment table 10 in two directions. In FIG. 1, a control unit controlling irradiation with a radiation r from the radiation sources 20 is not illustrated.

The radiation detector 30-1 detects a radiation r-1 which is emitted from the radiation source 20-1 and which arrives thereat through the body of the patient P and generates a radiographic image inside of the body of the patient P corresponding to the magnitude of energy of the detected radiation r-1. The radiation detector 30-2 detects a radiation r-2 which is emitted from the radiation source 20-2 and which arrives thereat through the body of the patient P and generates a radiographic image inside of the body of the patient P corresponding to the magnitude of energy of the detected radiation r-2.

Each of the radiation detectors 30 has X-ray detectors arranged in a two-dimensional array shape and generates a digital image in which the magnitude of energy of the radiation r arriving at each X-ray detector is expressed by a digital value as a radiographic image. The radiation detector 30 is, for example, a flat panel detector (FPD), an image intensifier, or a color image intensifier. In the following description, each of the radiation detectors 30 is an FPD. Each radiation detector 30 (FPD) outputs the generated radiographic image to the medical image processing device 100. In FIG. 1, a control unit that controls generation of a radiographic image in the radiation detectors 30 is not illustrated.

In FIG. 1, the configuration of the treatment system 1 including two imaging devices (pairs of the radiation source 20 and the radiation detector 30) is illustrated. However, the number of imaging devices included in the treatment system 1 is not limited to two. For example, the treatment system 1 may include three or more imaging devices (three or more pairs of the radiation source 20 and the radiation detector 30).

The treatment beam irradiation door 40 emits a radiation for destroying a lesion in the body of a patient P as a treatment beam B. The treatment beam B is, for example, an X-ray, a γ-ray, an electron beam, a photon beam, a neutron beam, or a baryon beam. The treatment beam B is linearly applied to a patient P (more specifically, a lesion in the body of the patient P) from the treatment beam irradiation door 40.

The irradiation control device 50 controls irradiation with the treatment beam B from the treatment beam irradiation door 40. The irradiation control device 50 causes the treatment beam irradiation door 40 to irradiate the patient P with the treatment B in response to an irradiation instruction signal which is output from the medical image processing device 100 and which indicates an irradiation timing of the treatment beam B.

In FIG. 1, the configuration of the treatment system 1 including one fixed treatment beam irradiation door 40 is illustrated, but the present invention is not limited thereto. The treatment system 1 may include a plurality of treatment beam irradiation doors. For example, the treatment system 1 may additionally include a treatment beam irradiation door that irradiates a patient P with a treatment beam in a horizontal direction. The treatment system 1 may have a configuration in which a patient P is irradiated with a treatment beam in various directions by causing one treatment beam irradiation door to rotate around the patient P. More specifically, the treatment beam irradiation door 40 illustrated in FIG. 1 may be configured to rotate 360° around a rotation axis in the horizontal direction Y illustrated in FIG. 1. The treatment system 1 having this configuration is called a rotary gantry type treatment system. In the rotary gantry type treatment system, the radiation source 20 and the radiation detector 30 rotate simultaneously 360° around the same axis as the rotation axis of the treatment beam irradiation door 40.

The medical image processing device 100 tracks a position of an object in the body of a patient P such as the lung or the liver which moves due to respiration or heartbeat of the patient P and determines an irradiation timing at which a lesion of the patient P is irradiated with the treatment B. The object in the body of the patient P is a metallic marker implanted in the body of the patient P, but the present invention is not limited thereto. For example, the object in the body of the patient P may be a lesion in the body of the patient P. In the following description, it is assumed that the object is a marker.

The medical image processing device 100 automatically determines an irradiation timing of the treatment beam B with which a lesion is irradiated by tracking an image of the marker in a radiographic image of the patient P captured in real time by the radiation detectors 30. At this time, the medical image processing device 100 determines whether a position of an image of the marker implanted in the body of the patient P being tracked is within a predetermined range in which radiation therapy is performed. Then, the medical image processing device 100 outputs an irradiation instruction signal indicating irradiation with the treatment B to the irradiation control device 50 when the position of the image of the marker is within the predetermined range. Accordingly, the irradiation control device 50 causes the treatment beam irradiation door 40 to emit the treatment beam B in response to the irradiation instruction signal output from the medical image processing device 100.

The medical image processing device 100 performs image processing for positioning of adjusting the current position of the patient P to a position determined in advance in a planning stage before radiation therapy is performed such as a stage of treatment planning. The medical image processing device 100 automatically retrieves a position of the patient P suitable for radiation therapy by combining a DRR image obtained by virtually reconstructing a radiographic image from a three-dimensional CT image captured in advance before radiation therapy is performed with current radiographic images output from the radiation detectors 30. Then, the medical image processing device 100 calculates an amount of movement of the treatment table 10 by which the current position of the patient P fixed on the treatment table 10 is moved to the suitable position determined in advance for the radiation therapy. Details of the configuration and the process of the medical image processing device 100 will be described later.

The medical image processing device 100 and the radiation detectors 30 may be connected via a local area network (LAN) or a wide area network (WAN).

The configuration of the medical image processing device 100 of the treatment system 1 will be described below. FIG. 2 is a block diagram schematically illustrating the configuration of the medical image processing device according to the first embodiment. The medical image processing device 100 illustrated in FIG. 2 includes a first image acquiring unit

101, a first likelihood distribution calculating unit 102, a trackability determining unit 103, a tracking unit 104, a second image acquiring unit 105, and a second likelihood distribution calculating unit 106.

The first image acquiring unit 101 acquires a plurality of first images which are transparent images of a patient P and which have different imaging directions. Each of the first images may be a radiographic image captured by the radiation detector 30 in positioning the patient P or may be a DRR image obtained by virtually reconstructing a radiographic image from a three-dimensional CT image captured in advance before radiation therapy is performed.

The first likelihood distribution calculating unit 102 calculates a first likelihood distribution indicating a distribution of likelihoods indicating a likeness to a marker (an object) in each of the plurality of first images 60 acquired by the first image acquiring unit 101.

Figure 3:
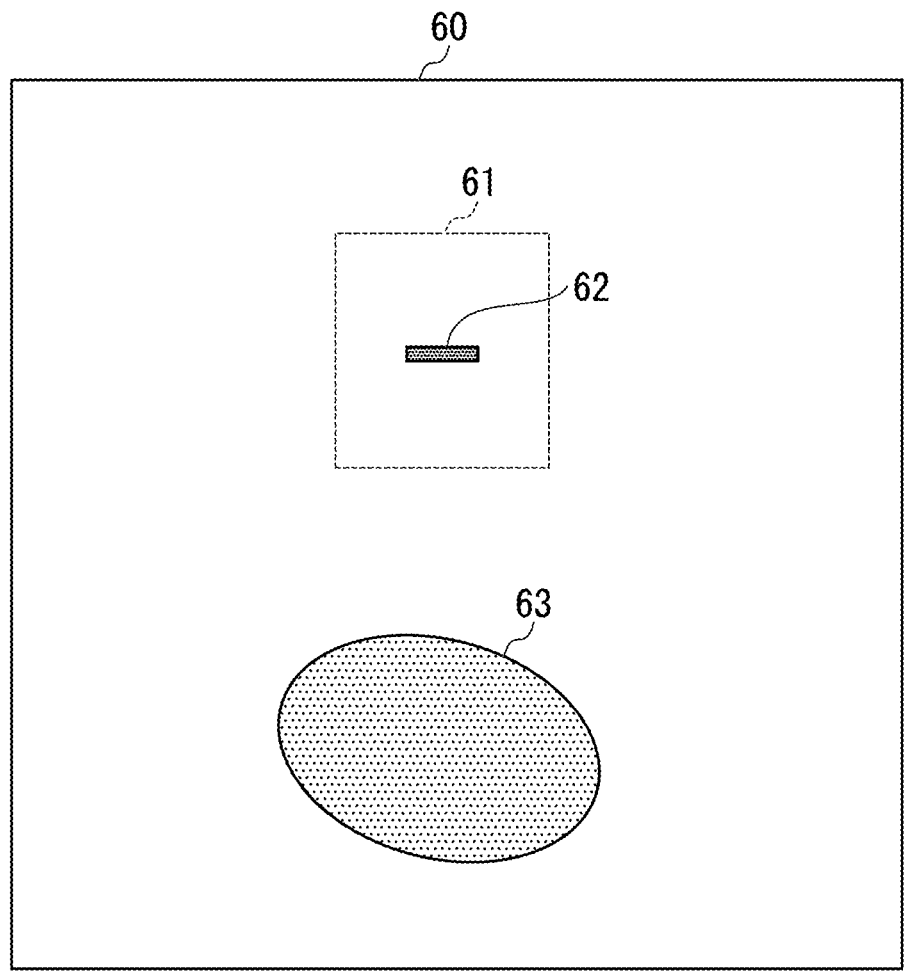
FIG. 3 is a diagram illustrating an example of a first image according to the first embodiment.

FIG. 3 is a diagram illustrating an example of the first image according to the first embodiment. The first image 60 includes an image of a marker 62 implanted in the body of a patient P and an image of a lesion 63 in the body of the patient P. The first likelihood distribution calculating unit 102 does not calculate a likelihood distribution in the whole first image 60 but calculates a likelihood distribution in a tracking area 61. The tracking area 61 is an area in which the position of the marker 62 is tracked and is an area including a range in which the marker 62 moves due to respiration or heartbeat of the patient P. In this way, by limiting a target for which the first likelihood distribution is calculated to a part (tracking area 61) in the first image 60, it is possible to reduce a processing load of the first likelihood distribution calculating unit 102.

For example, the tracking area 61 is determined on the basis of the position of the marker 62 designated in a CT image at the time of treatment planning. The tracking area 61 is determined in consideration of a margin based on an error which is likely to occur during actual treatment. For example, the tracking area 61 may be an area obtained by projecting a three-dimensional area with a margin around the position of the marker 62 in the CT image onto the first image. The tracking area 61 may be determined according to a margin determined in consideration of a state of the patient immediately before treatment.

In FIG. 3, the marker 62 has a rod shape, but the shape of the maker 62 is not limited thereto. For example, the marker may have a spherical shape.

A method of calculating a likelihood in the first likelihood distribution calculating unit 102 will be described below. The first likelihood distribution calculating unit 102 stores an image pattern when the marker 62 has been projected as a template image in advance and calculates a likelihood by calculating a degree of similarity between the first image 60 and the template image.

When a shadow shape of the maker 62 can be expected in advance such as when the marker 62 has a spherical shape, an image in which the shadow is drawn may be used as the template image. When the shadow of the marker 62 changes according to a posture of the marker 62 when the marker is implanted in the body of the patient P, a plurality of template images in which a shadow corresponding to the posture of the marker 62 is drawn may be generated and one of the plurality of template images may be selected and used.

The degree of similarity which is a numerical value of the likelihood is expressed by pixel values or a spatial correlation value between the template image and the first image 60. For example, the degree of similarity may be a reciprocal of a difference in pixel value between the corresponding pixel positions. The degree of similarity may be a mutual correlation value between the corresponding pixel positions.

The first likelihood distribution calculating unit 102 may generate a discriminator on the basis of a machine learning method using a template image including the marker 62 as training data and calculate the likelihood using the generated discriminator. For example, a discriminator is generated by preparing a template image including the marker 62 and a plurality of first images 60 of positions not including the marker 62 and learning the images using the machine learning method. It is possible to ascertain whether the marker 62 is included using the generated discriminator.

A support-vector machine, a random forest, a deep learning, or the like may be used as the machine learning method. The first likelihood distribution calculating unit 102 calculates a real number value calculated using the machine learning method as a likelihood. For example, a distance to a discrimination boundary, a ratio of discriminators having determined to include an object, or an output value of Softmax may be used as the real number value.

Figure 4:
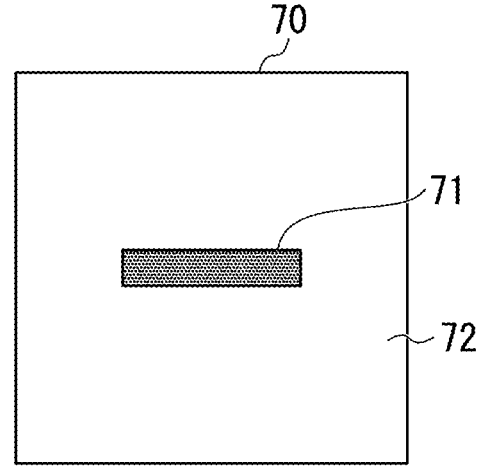
FIG. 4 is a diagram illustrating an example of a template that is used to calculate a degree of separation according to the first embodiment.

The first likelihood distribution calculating unit 102 may calculate the likelihood using a degree of separation. FIG. 4 is a diagram illustrating an example of a template which is used to calculate a degree of separation according to the first embodiment. In the example of a template 70 illustrated in FIG. 4, the template is divided into a first area 71 in which a rod-shaped marker 62 is present and a second area 72 other than the first area 71. That is, the second area 72 is an area in which the rod-shaped marker 62 is not present.

In calculating the degree of separation, when the same area as the template 70 is present in the first image 60, histograms of pixel values included in the first image 60 are classified into a histogram of pixel values belonging to the first area 71 and a histogram of pixels values belonging to the second area 72. This is because, when an image of the marker 62 included in the first image 60 overlaps the first area 71, a histogram of pixel values belonging to the first area 71 has an increasing frequency of pixel values of dark pixels and a histogram of pixel values belonging to the second area 72 has an increasing frequency of pixel values of bright pixels.

The first likelihood distribution calculating unit 102 digitalizes separation of the histograms of pixel values using Fischer's determination criteria. Then, the first likelihood distribution calculating unit 102 calculates a ratio of an average of variances of pixel values of pixels belonging to the areas (intra-class variance) and a variance of pixel values between the areas (inter-class variance) and calculates the ratio as a degree of separation. In this way, the first likelihood distribution calculating unit 102 calculates the degree of separation calculated using the template 70 as a likelihood. The first likelihood distribution calculating unit 102 calculates a first likelihood distribution indicating a distribution of likelihoods in a plurality of first images 60 acquired by the first image acquiring unit 101 using the calculated likelihoods.

The trackability determining unit 103 determines whether the marker 62 is trackable on the basis of the first likelihood distribution calculated by the first likelihood distribution calculating unit 102. Specifically, the trackability determining unit 103 calculates a degree of tracking difficulty in imaging directions of the first images 60 on the basis of the first likelihood distribution calculated by the first likelihood distribution calculating unit 102. When the degree of tracking difficulty is higher than a predetermined threshold value, the trackability determining unit 103 determines that the marker 62 is not trackable.

The trackability determining unit 103 calculates the degree of tracking difficulty on the basis of a statistic of the first likelihood distribution. The statistic is, for example, a primary statistic such as an average of the first likelihood distribution or a variance of the first likelihood distribution, but the present invention is not limited thereto. For example, the statistic may be a maximum value of the first likelihood distribution or may be a value using a linear equation into which such numerical values are combined. When the position of the marker 62 corresponding to the first likelihood distribution is acquired, the trackability determining unit 103 may calculate the degree of tracking difficulty by narrowing to the statistic of the first likelihood distribution near the position of the marker 62. The trackability determining unit 103 outputs the results of determination of trackability of the marker 62 in the imaging directions to the tracking unit 104 and the second image acquiring unit 105.

The tracking unit 104 tracks the position of the marker 62 in a second image acquired by the second image acquiring unit 105 on the basis of the results of determination from the trackability determining unit 103. Details of the tracking process in the tracking unit 104 will be described later.

The second image acquiring unit 105 acquires a plurality of second images which are transparent images of the patient P generated at times different from that of the first images and which have different imaging directions. The first images are transparent images generated on the basis of a three-dimensional image of the patient P captured at the time of treatment planning or transparent images captured in the same imaging directions as the second images immediately before treatment, and the second images are transparent images captured by the radiation detectors 30 during treatment of the patient P. The second images are repeatedly captured at intervals of a predetermined time to track the marker 62.

It is preferable that the imaging directions of the first images be the same as the imaging directions of the second images. For example, when the second image is captured in a direction different from that at the time of positioning the patient P, the first images are not transparent images captured at the time of positioning the patient P, but DDR images obtained by simulating transparent images captured in the same directions as the second images. The first images may be the second images captured at the time of previous treatment or may be images captured in the same directions as the second images immediately before treatment. The first images may be a moving image in one or more cycles of respiration.

The second image acquiring unit 105 determines imaging directions of second images used for the tracking unit 104 to track the position of the marker 62 on the basis of the results of determination from the trackability determining unit 103 before treatment using irradiation with the treatment beam B is performed on the patient P. For example, when a result of determination for the first image in the imaging direction of the radiation detector 30-1 is "trackable" and a result of determination for the first image in the imaging direction of the radiation detector 30-2 is "trackable," the second image acquiring unit 105 acquires both a second image captured by the radiation detector 30-1 and a second image captured by the radiation detector 30-2. When a result of determination for the first image in the imaging direction of the radiation detector 30-1 is "trackable" and a result of determination for the first image in the imaging direction of the radiation detector 30-2 is "non-trackable," the second image acquiring unit 105 acquires only a second image captured by the radiation detector 30-1. When a result of determination for the first image in the imaging direction of the radiation detector 30-1 is "non-trackable" and a result of determination for the first image in the imaging direction of the radiation detector 30-2 is "trackable," the second image acquiring unit 105 acquires only a second image captured by the radiation detector 30-2.

In this way, since the second image acquiring unit 105 does not acquire a second image in the imaging direction in which the marker 62 is determined to be non-trackable, it is possible to curb radiation exposure of the patient P and to improve a tracking success rate of the marker 62.

The second likelihood distribution calculating unit 106 calculates a second likelihood distribution indicating a distribution of likelihoods in a second image acquired by the second image acquiring unit 105. Here, the second likelihood distribution calculating unit 106 does not calculate the second likelihood distribution in the whole second image, but calculates the second likelihood distribution in a tracking area 61 in the second image. The method of calculating the second likelihood distribution is the same as the method of calculating the first likelihood distribution and thus description thereof will be omitted.

The tracking unit 104 determines a position of the marker 62 in the second image on the basis of the second likelihood distribution calculated by the second likelihood distribution calculating unit 106. For example, the tracking unit 104 determines that a position of a maximum value in the second likelihood distribution is the position of the marker 62.

When the second images are acquired in two directions and the position of the marker 62 in one second image is identified, the position of the marker 62 in the other second image is geometrically limited to an epipolar line. Therefore, the tracking unit 104 may determine that a position of a maximum value of the likelihood distribution on the epipolar line in the second likelihood distribution of the other second image is the position of the marker 62. When the second images are acquired in two directions, the tracking unit 104 may geometrically convert the position of the marker 62 to a three-dimensional coordinate system and calculate the position of the marker 62.

The tracking unit 104 determines an irradiation timing of the treatment beam B on the basis of the determined position of the marker 62. A positional relationship between a marker 62 and a lesion 63 can be identified from a transparent image of the patient P acquired at the time of treatment planning. Accordingly, when a position of the lesion 63 in the body of the patient P identified on the basis of the position of the marker 62 is located in a predetermined range, the tracking unit 104 transmits an irradiation instruction signal instructing irradiation with the treatment beam B to the irradiation control device 50.

The irradiation control device 50 causes the treatment beam irradiation door 40 to emit the treatment beam B in response to the irradiation instruction signal received from the medical image processing device 100. Accordingly, it is possible to irradiate the lesion 63 in the body of the patient P with the treatment beam B.

On the other hand, when the position of the lesion 63 in the body of the patient P identified on the basis of the position of the marker 62 is not in the predetermined range, the tracking unit 104 does not transmit the irradiation instruction signal to the irradiation control device 50. Accordingly, it is possible to curb irradiation of a region other than the lesion 63 with the treatment beam B.

For example, the medical image processing device 100 may include a hardware processor such as a central processing unit (CPU) and a storage device (a storage device including a non-transitory storage medium) storing a program (software), and some or all of the functions of the constituents provided therein may be realized by causing the processor to execute the program. Some or all of the functions of the constituents of the medical image processing device 100 may be realized by hardware (a circuit unit including circuitry) such as a large-scale integration (LSI), an application-specific integrated circuit (ASIC), a field-programmable gate array (FPGA), or a graphics processing unit (GPU), or various functions may be cooperatively realized by software and hardware. Some or all of the functions of the constituents provided in the medical image processing device 100 may be realized by a dedicated LSI.

Here, the program (software) may be stored in a storage device (a storage device including a non-transitory storage medium) provided in the treatment system 1 such as a read only memory (ROM), a random access memory (RAM), a hard disk drive (HDD), or a flash memory, or may be stored in a removable storage medium (a non-transitory storage medium) such as a DVD or a CD-ROM and installed in the storage device provided in the treatment system 1 by installing the storage medium in a drive device provided in the treatment system 1. The program (software) may be downloaded in advance from another computer device via a network and installed in the storage device provided in the treatment system 1.

Figure 5:
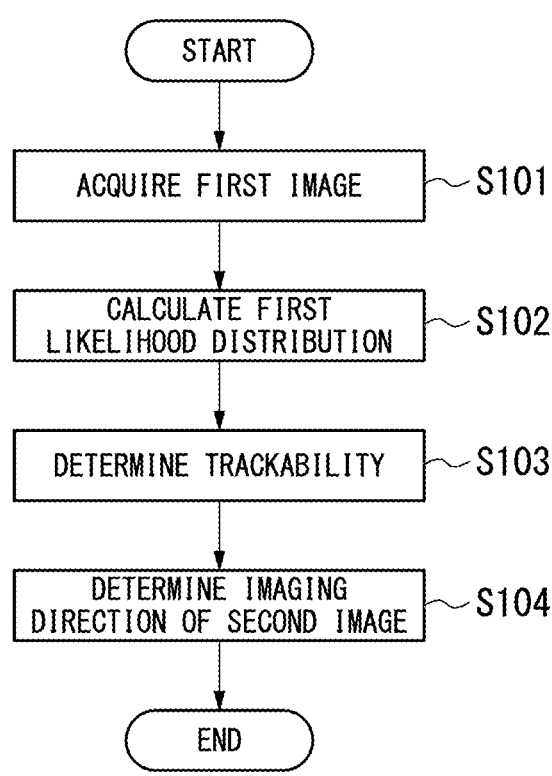
FIG. 5 is a flowchart illustrating a routine of operations of the medical image processing device in a stage before a patient is treated according to the first embodiment.

FIG. 5 is a flowchart illustrating a routine of operations of the medical image processing device in a stage before a patient is treated according to the first embodiment. The routine in the flowchart is performed by the medical image processing device 100 in a stage before treatment using irradiation with a treatment beam B is performed on a patient P.

First, the first image acquiring unit 101 acquires a plurality of first images which are transparent images of the patient P and which have different imaging directions (S101). As described above, each of the first images may be a radiographic image captured by the radiation detector 30 in positioning the patient P or may be a DRR image obtained by virtually reconstructing a radiographic image from three-dimensional CT images captured in advance before radiation therapy is performed.

Then, the first likelihood distribution calculating unit 102 calculates a first likelihood distribution indicating a distribution of likelihoods indicating a likeness to a marker (object) in each of the plurality of first images 60 acquired by the first image acquiring unit 101 (S102). Here, the first likelihood distribution calculating unit 102 does not calculate a likelihood distribution in the whole first image 60, but calculates a likelihood distribution in the tracking area 61 illustrated in FIG. 3.

Then, the trackability determining unit 103 determines whether the marker 62 is trackable on the basis of the first likelihood distribution calculated by the first likelihood distribution calculating unit 102 (S103). For example, the trackability determining unit 103 calculates a degree of tracking difficulty in each imaging direction of the first images 60 on the basis of the first likelihood distribution calculated by the first likelihood distribution calculating unit 102. When the degree of tracking difficulty is higher than a predetermined threshold value, the trackability determining unit 103 determines that the marker 62 is not trackable.

Thereafter, the second image acquiring unit 105 determines an imaging direction of a second image on the basis of the result of determination from the trackability determining unit 103 (S104) and then ends the routine of the flowchart. When treatment using irradiation with a treatment beam B is performed on the patient P, the marker 62 is tracked on the basis of the second image corresponding to the imaging direction determined in Step S104.

Figure 6:
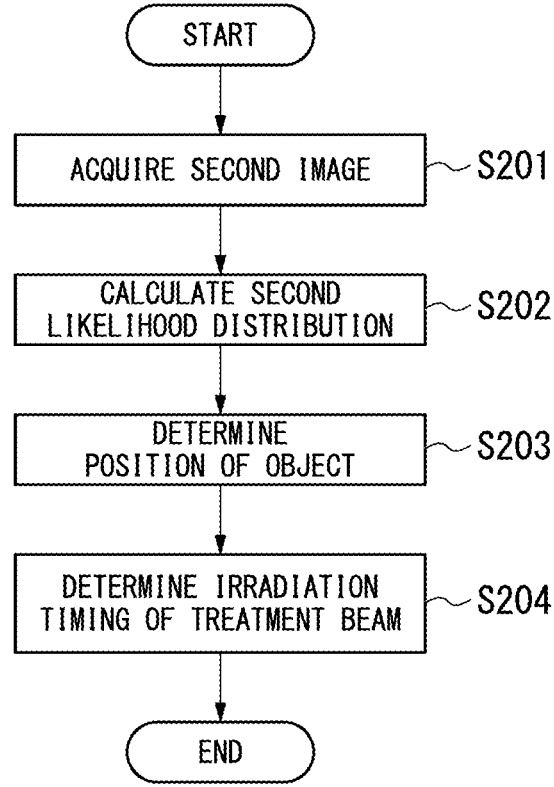
FIG. 6 is a flowchart illustrating a routine of operations of the medical image processing device in a stage when a patient is being treated according to the first embodiment.

FIG. 6 is a flowchart illustrating a routine of operations of the medical image processing device in a stage when a patient is being treated according to the first embodiment. The routine of the flowchart is repeatedly performed at intervals of a predetermined time by the medical image processing device 100 in the stage when treatment using irradiation with a treatment beam B is performed on a patient P.

First, the second image acquiring unit 105 acquires a second image corresponding to the imaging direction determined in Step S104 (S201). The second image is an image captured by the radiation detector 30 during treatment of the patient P. Specifically, the second image acquiring unit 105 does not acquire the second image in an imaging direction in which the degree of tracking difficulty is higher than a predetermined threshold value, but acquires only the second image in an imaging direction in which the degree of tracking difficulty is equal to or lower than the predetermined threshold value.

Then, the second likelihood distribution calculating unit 106 calculates a second likelihood distribution indicating a distribution of likelihoods in the second images acquired by the second image acquiring unit 105 (S202). The method of calculating the second likelihood distribution is the same as the method of calculating the first likelihood distribution.

Then, the tracking unit 104 determines a position of the marker 62 (object) in the second image on the basis of the second likelihood distribution calculated by the second likelihood distribution calculating unit 106 (S203). For example, the tracking unit 104 determines that a position of a maximum value in the second likelihood distribution is the position of the marker 62.

Thereafter, the tracking unit 104 determines an irradiation timing of the treatment beam B on the basis of the determined position of the marker 62 (object) (S204). For example, when the position of the lesion 63 in the body of the patient P identified on the basis of the position of the marker 62 is located in a predetermined range, the tracking unit 104 transmits an irradiation instruction signal indicating irradiation with the treatment beam B to the irradiation control device 50. The irradiation control device 50 causes the treatment beam irradiation door 40 to emit the treatment beam B in response to the irradiation instruction signal received from the medical image processing device 100.

As described above, in the first embodiment, the first image acquiring unit 101 acquires a plurality of first images which are transparent images of a patient P and which have different imaging directions. The second image acquiring unit 105 acquires a plurality of second images which are transparent images of the patient P generated at times different from that of the first images and which have different imaging directions. The first likelihood distribution calculating unit 102 calculates a first likelihood distribution indicating a distribution of likelihoods indicating a likeness to an object in the plurality of first images acquired by the first image acquiring unit 101. The trackability determining unit 103 determines whether the object is trackable on the basis of the first likelihood distribution calculated by the first likelihood distribution calculating unit 102. The tracking unit 104 tracks a position of the object in the second images acquired by the second image acquiring unit 105 on the basis of the result of determination from the trackability determining unit 103. Accordingly, it is possible to highly precisely track an object in the body of a patient from transparent images of the patient.

Second Embodiment

In the first embodiment, the second image acquiring unit 105 determines an imaging direction of a second image on the basis of a result of determination from the trackability determining unit 103. On the other hand, in a second embodiment, the tracking unit 104 determines a tracking area which is an area in which a position of an object is tracked on the basis of the result of determination from the trackability determining unit 103. Accordingly, it is possible to more highly precisely track an object in the body of a patient. The second embodiment will be described below in detail.

FIG. 7 is a block diagram schematically illustrating a configuration of a medical image processing device according to the second embodiment. In FIG. 7, elements corresponding to the constituent units illustrated in FIG. 2 will be referred to by the same reference signs and description thereof will not be repeated.

The trackability determining unit 103 determines whether a marker 62 is trackable on the basis of a first likelihood distribution calculated by the first likelihood distribution calculating unit 102. Specifically, the trackability determining unit 103 calculates a degree of tracking difficulty in each imaging direction of the first images 60 on the basis of the first likelihood distribution calculated by the first likelihood distribution calculating unit 102. The method of calculating the degree of tracking difficulty is the same as in the first embodiment and thus description thereof will be omitted. When the degree of tracking difficulty is higher than a predetermined threshold value, the trackability determining unit 103 determines that the marker 62 is not trackable. Thereafter, the trackability determining unit 103 outputs a result of determination of whether the marker 62 is trackable in each imaging direction to the tracking unit 104. On the other hand, unlike the first embodiment, the trackability determining unit 103 does not output the result of determination to the second image acquiring unit 105.

The second image acquiring unit 105 acquires a plurality of second images which are transparent images of a patient P generated at a time different from that of the first images and which have different imaging directions. For example, the second images are images captured by the radiation detectors 30 during treatment of the patient P. Specifically, the second image acquiring unit 105 acquires both a transparent image captured by the radiation detector 30-1 and a transparent image captured by the radiation detector 30-2 as the second images.

The second likelihood distribution calculating unit 106 calculates a second likelihood distribution indicating a distribution of likelihoods in the second images acquired by the second image acquiring unit 105. Specifically, the second likelihood distribution calculating unit 106 calculates a distribution of likelihoods in the transparent image (the second image) captured by the radiation detector 30-1 and a distribution of likelihoods in the transparent image (the second image) captured by the radiation detector 30-2 as the second likelihood distribution. Here, the second likelihood distribution calculating unit 106 does not calculate the second likelihood distribution in the whole second image, but calculates the second likelihood distribution in a tracking area 61 of the second image. The method of calculating the second likelihood distribution is the same as the method of calculating the first likelihood distribution and thus description thereof will be omitted.

The tracking unit 104 determines a tracking area 61 (FIG. 3) which is an area in which the position of the marker 62 is tracked on the basis of the result of determination from the trackability determining unit 103. Specifically, the tracking unit 104 limits the tracking area 61 to an area on an epipolar line in the second image of the imaging direction in which the degree of tracking difficulty of the marker 62 is determined to be higher than the predetermined threshold value by the trackability determining unit 103.

For example, it is assumed that the degree of tracking difficulty in the imaging direction of the radiation detector 30-1 is higher than the predetermined threshold value and the degree of tracking difficulty in the imaging direction of the radiation detector 30-2 is equal to or lower than the predetermined threshold value. In this case, when the position of the marker 62 is identified from the second image captured by the radiation detector 30-2, the position of the marker 62 in the second image captured by the radiation detector 30-1 is geometrically limited to an area on the epipolar line. Accordingly, the tracking unit 104 limits the tracking area 61 to an area on the epipolar line in the second image captured by the radiation detector 30-1.

In this way, an imaging direction in which the marker 62 can be easily tracked is determined on the basis of the degree of tracking difficulty, and the tracking area 61 for the second image in the imaging direction in which tracking is difficult is limited to an area on the epipolar line to track the marker 62. Accordingly, with a medical image processing device 200 according to this embodiment, it is possible to improve tracking accuracy of the marker 62.

Figure 8:
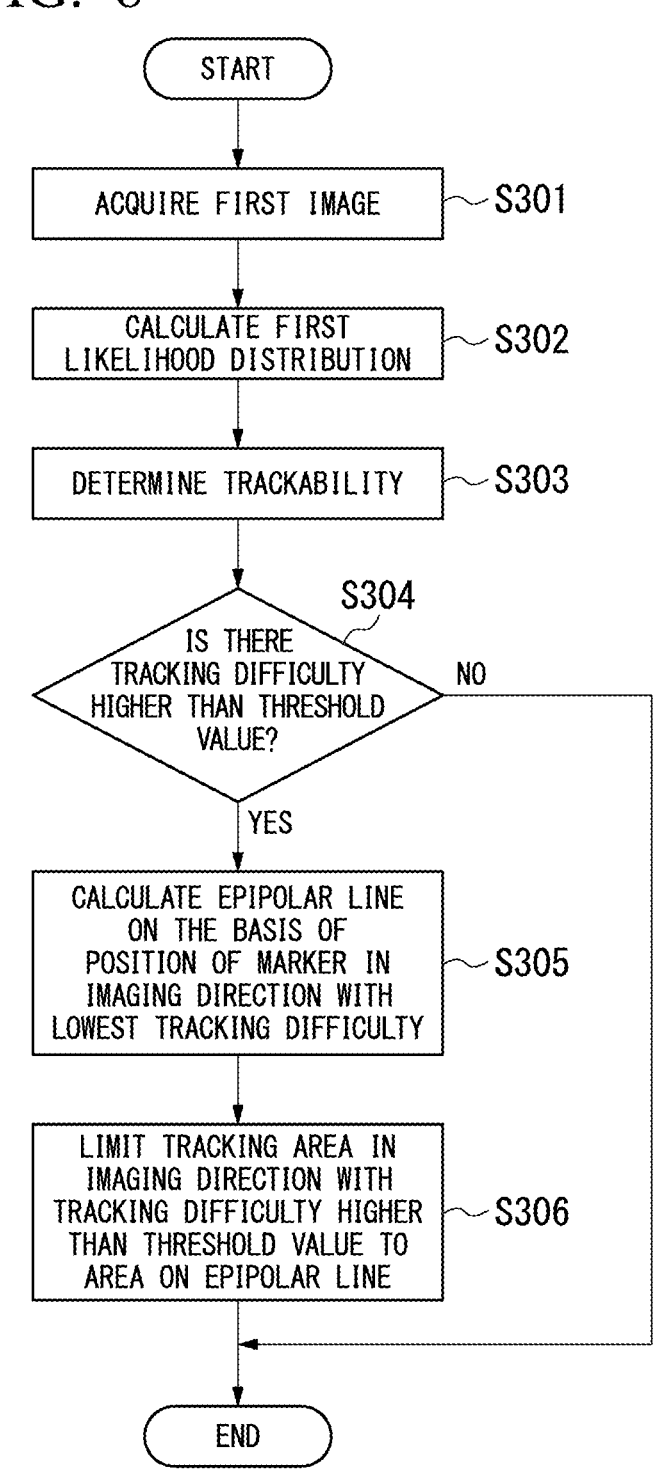
FIG. 8 is a flowchart illustrating a routine of operations of the medical image processing device in a stage before a patient is treated according to the second embodiment.

FIG. 8 is a flowchart illustrating a routine of operations of the medical image processing device in a stage before a patient is treated according to the second embodiment. The routine of the flowchart is performed by the medical image processing device 200 in a stage before treatment using irradiation with a treatment beam B is performed on a patient P. Steps S301 to S303 in FIG. 8 are the same as Steps S101 to S103 in FIG. 5 and thus description thereof will be omitted.

The trackability determining unit 103 determines whether there is a degree of tracking difficulty higher than the predetermined threshold value in the degrees of tracking difficulty in the imaging directions calculated in Step S303 (S304). When there is not a degree of tracking difficulty higher than the predetermined threshold value (S304: NO), the tracking unit 104 does not change the tracking area 61 and ends the routine of the flowchart. On the other hand, when there is a degree of tracking difficulty higher than the predetermined threshold value (S304: YES), the tracking unit 104 calculates a straight line connecting the position of the marker 62 in the imaging direction in which the degree of tracking difficulty is the lowest and an imaging position (the position of the radiation detector 30) in the imaging direction in which the degree of tracking difficulty is the lowest as an epipolar line (S305). Thereafter, the tracking unit 104 limits the tracking area 61 in the imaging direction in which the degree of tracking difficulty is higher than the predetermined threshold value to an area on the epipolar line calculated in Step S305 (S306) and ends the routine of the flowchart.

In this way, the tracking unit 104 does not change the tracking area 61 in the second image in the imaging direction in which the degree of tracking difficulty is equal to or lower than the predetermined threshold value. On the other hand, regarding the second image in the imaging direction in which the degree of tracking difficulty is determined to be higher than the predetermined threshold value, the tracking unit 104 limits the tracking area 61 to an area on the epipolar line calculated on the basis of the position of the marker 62 in the imaging direction in which the degree of tracking difficulty is the lowest. Accordingly, with the medical image processing device 200 according to this embodiment, it is possible to improve tracking accuracy of the marker 62.

Third Embodiment

In the first embodiment and the second embodiment, the irradiation control device 50 that controls the treatment beam irradiation door 40 is provided. On the other hand, in a third embodiment, it is assumed that the irradiation control device 50 is not provided in the treatment system 1, but a radiation therapy device 300 has a function of controlling the treatment beam irradiation door 40. The third embodiment will be described below in detail.

Figure 9:
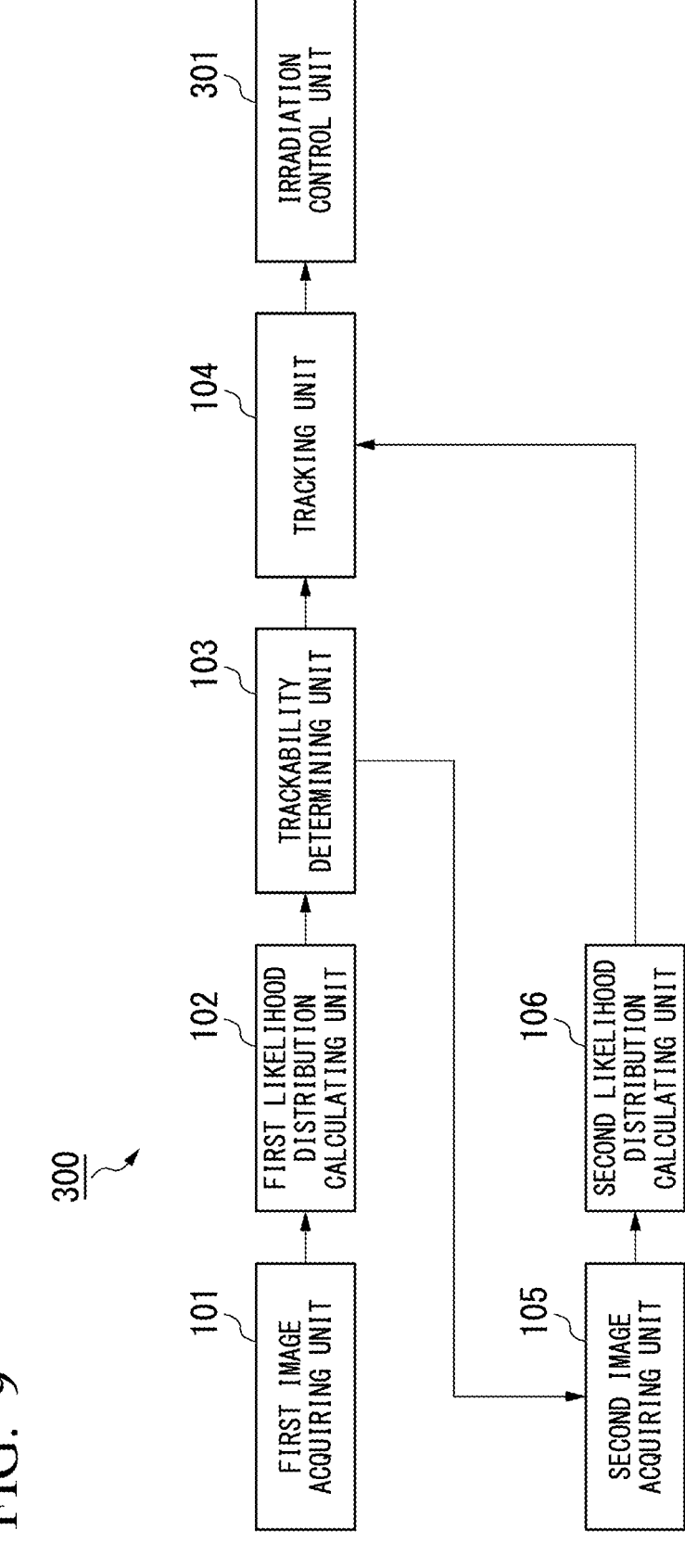
FIG. 9 is a block diagram schematically illustrating a configuration of a radiation therapy device according to a third embodiment.

FIG. 9 is a block diagram schematically illustrating a configuration of a radiation therapy device according to a third embodiment. In FIG. 9, elements corresponding to the constituents in FIG. 2 will be referred to by the same reference signs and description thereof will not be repeated. The radiation therapy device 300 according to the third embodiment includes an irradiation control unit 301.

The tracking unit 104 determines a position of a marker 62 in a second image on the basis of a second likelihood distribution calculated by the second likelihood distribution calculating unit 106. For example, the tracking unit 104 determines that a position of a maximum value in the second likelihood distribution is the position of the marker 62.

The tracking unit 104 determines an irradiation timing of a treatment beam B on the basis of the determined position of the marker 62. The positional relationship between the marker 62 and the lesion 63 can be identified from transparent images of a patient P acquired at the time of treatment planning. Accordingly, when the position of the lesion 63 in the body of the patient P identified on the basis of the position of the marker 62 is located in a predetermined range, the tracking unit 104 outputs an irradiation instruction signal indicating irradiation with a treatment beam B to the irradiation control unit 301.

The irradiation control unit 301 causes the treatment beam irradiation door 40 to emit the treatment beam B in response to the irradiation instruction signal output from the tracking unit 104. Accordingly, it is possible to irradiate the lesion 63 in the body of the patient P with the treatment beam B.

On the other hand, when the position of the lesion 63 in the body of the patient P identified on the basis of the position of the marker 62 is not located in the predetermined range, the tracking unit 104 does not output the irradiation instruction signal to the irradiation control unit 301. Accordingly, it is possible to curb irradiation of a region other than the lesion 63 with the treatment beam B.

Figure 10:
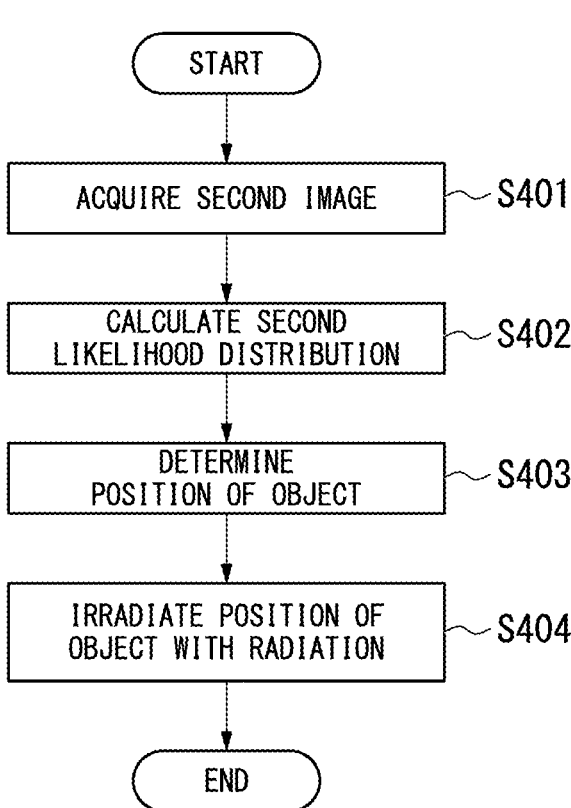
FIG. 10 is a flowchart illustrating a routine of operations of the radiation therapy device in a stage when a patient is being treated according to the third embodiment.

FIG. 10 is a flowchart illustrating a routine of operations of a radiation therapy device in a stage when a patient is being treated according to the third embodiment. The routine of the flowchart is repeatedly performed at intervals of a predetermined time by the radiation therapy device 300 in a stage in which treatment using irradiation with a treatment beam B is being performed on a patient P. Steps S401 to S403 in FIG. 10 are the same as Steps S201 to S203 in FIG. 6 and thus description thereof will be omitted.

The irradiation control unit 301 causes the treatment beam irradiation door 40 to emit a treatment beam B according to the position of the marker 62 (object) determined by the tracking unit 104 in Step S403. For example, when the position of the lesion 63 in the patient P identified on the basis of the position of the marker 62 is located in a predetermined range, the irradiation control unit 301 causes the treatment beam irradiation door 40 to emit a treatment beam B.

In this way, the radiation therapy device 300 according to the third embodiment includes the irradiation control unit 301 that controls the treatment beam irradiation door in addition to the functions of the medical image processing device 100 according to the first embodiment. With the radiation therapy device 300 according to this embodiment, similarly to the first embodiment, it is possible to improve tracking accuracy of the marker 62.

In the aforementioned embodiments, an object which is tracked by the tracking unit 104 is a metallic marker implanted in the body of a patient P, but the object may be lesion in the body of the patient P. In this case, an image including the whole lesion or a part of the lesion may be trimmed from the first image and the trimmed image may be used as a template image. When the first image is a DRR image generated from a CT image including treatment plan information, a position of a lesion in the CT image is included in the treatment plan information and thus an image onto which the lesion is projected may be used as a template image. When the first image is a radiographic image captured by the radiation detector 30 in positioning of the patient P, the position of the patient P matches the DRR image and thus a radiographic image near the lesion may be trimmed using the position of the lesion and the trimmed image may be used as a template image.

The trackability determining unit 103 may present the degrees of tracking difficulty in the imaging directions to a user using a notification unit (not illustrated). For example, the trackability determining unit 103 may notify of the imaging direction in which the degree of tracking difficulty is low when a user plans the imaging directions. Accordingly, the user can predict a success rate of the respiration-synchronized irradiation method or determine whether tracking of the marker 62 is to be performed on only a second image in one imaging direction.

The medical image processing devices 100 and 200 and the radiation therapy device 300 can be realized, for example, by using a general-purpose computer device as basic hardware. That is, the first image acquiring unit 101, the first likelihood distribution calculating unit 102, the trackability determining unit 103, the tracking unit 104, the second image acquiring unit 105, the second likelihood distribution calculating unit 106, and the irradiation control unit 301 can be realized by causing a processor provided in the computer device to execute a program. At this time, the medical image processing devices 100 and 200 and the radiation therapy device 300 may be realized by installing the program in the computer device in advance or may be realized by storing the program in a storage medium such as a CD-ROM or distributing the program via a network and appropriately installing the program in the computer device. B and C can be realized by appropriately using a memory incorporated into or externally attached to the computer device, a hard disk, or a storage medium such as CD-R, a CD-RW, a DVD-RAM, or a DVD-R.

While some embodiments of the present invention have been described above, these embodiments are presented merely as examples and are not intended to limit the scope of the present invention. The embodiments can be modified in various forms, and can be subjected to various omissions, substitutions, and modifications without departing from the gist of the present invention. The embodiments or modifications thereof are included in the scope or gist of the present invention and are also included in the inventions described in the appended claims and scopes equivalent thereto.

REFERENCE SIGNS LIST

1 . . . Treatment system
100 . . . Medical image processing device
101 . . . First image acquiring unit
102 . . . First likelihood distribution calculating unit
103 . . . Trackability determining unit
104 . . . Tracking unit
105 . . . Second image acquiring unit
106 . . . Second likelihood distribution calculating unit
200 . . . Medical image processing device
300 . . . Radiation therapy device
301 . . . Irradiation control unit

The invention claimed is:

1. A medical image processing device tracking a position of an object in a patient's body, the medical image processing device comprising a processor configured to:

acquire a plurality of first images which are transparent images of the patient and of which imaging directions are different;

calculate, for each of the plurality of first images, a degree of similarity at each pixel position with respect to the object as a likelihood representing a likeness to the object, and calculate a first likelihood distribution indicating a distribution of likelihoods in the first image;

determine whether the object is trackable for each of the plurality of first images on the basis of the first likelihood distribution;

in response to determining that the object is trackable for each of the plurality of first images, acquire a plurality of second images which are transparent images of the patient generated at a time different from that of the plurality of first images and of which imaging directions are the same as those of the plurality of first images, and in response to determining that the object is trackable for one or more first images among the plurality of first images and that the object is not trackable for remaining one or more first images, acquire the plurality of second images which are transparent images of the patient generated at a time different from that of the one or more first images and of which imaging directions are the same as those of the one or more first images, and not acquiring remaining one or more second images which are transparent images of the patient generated at a time different from that of the remaining one or more first images and of which imaging directions are the same as those of the remaining one or more first images;

calculate, for each of the plurality of second images, a degree of similarity at each pixel position with respect to the object as the likelihood representing a likeness to the object, and calculate a second likelihood distribution indicating a distribution of the likelihood in the second image;

determine a position of the object in the second image based on the second likelihood distribution, and track the position of the object;

control irradiation with the radiation according to the position of the object; and

determine an imaging direction of the plurality of second images which are used to track the position of the object before the patient is treated.

2. The medical image processing device according to claim 1, wherein the processor is configured to determine a tracking area which is an area in which the position of the object is tracked on the basis of a result of determination whether the object is trackable.

3. The medical image processing device according to claim 2, wherein the processor is configured to calculate a degree of tracking difficulty indicating a degree of difficulty of tracking the object in the plurality of second images, and wherein the processor is configured to limit the tracking area to an area on an epipolar line in the plurality of second images of which the degree of tracking difficulty is higher than a predetermined threshold value.

4. The medical image processing device according to claim 1, wherein the object is a metallic marker.

5. The medical image processing device according to claim 1, wherein the first image is a transparent image which is generated on the basis of a three-dimensional image of the patient captured at a time of treatment planning or a transparent image which is captured in the same imaging direction as the second image immediately before treatment, and wherein the second image is a transparent image which is captured during the treatment of the patient.

6. A medical image processing method of tracking a position of an object in a patient's body, the medical image processing method being performed by a processor and comprising:

a first image acquiring step of acquiring a plurality of first images which are transparent images of the patient and of which imaging directions are different;

a first likelihood distribution calculating step of calculating, for each of the plurality of first images, a degree of similarity at each pixel position with respect to the object as a likelihood representing a likeness to the object, and calculating a first likelihood distribution indicating a distribution of likelihoods in the first image;

a trackability determining step of determining whether the object is trackable for each of the plurality of first images on the basis of the first likelihood distribution;

a second image acquiring step of acquiring a plurality of second images, wherein the second image acquiring step comprises:

in response to determining that the object is trackable for each of the plurality of first images, acquiring the plurality of second images which are transparent images of the patient generated at a time different from that of the plurality of first images and of which imaging directions are the same as those of the plurality of first images, and in response to determining that the object is trackable for one or more first images among the plurality of first images, acquiring the plurality of second images which are transparent images of the patient generated at a time different from that of the one or more first images and of which imaging directions are the same as those of the one or more first images, and not acquiring remaining one or more second images which are transparent images of the patient generated at a time different from that of the remaining one or more first images and of which imaging directions are the same as those of the remaining one or more first images;

a calculating step of calculating, for each of the plurality of second images, a degree of similarity at each pixel position with respect to the object as the likelihood representing a likeness to the object, and calculating a second likelihood distribution indicating a distribution of the likelihood in the second image;

a tracking step of determining a position of the object in the second image based on the second likelihood distribution, and tracking the position of the object; and a step of controlling irradiation with the radiation according to the position of the object.

7. A non-transitory computer readable storage medium storing a medical image processing program for tracking a position of an object in a patient's body, the medical image processing program causing a computer to perform:

a first image acquiring step of acquiring a plurality of first images which are transparent images of the patient and of which imaging directions are different;

a first likelihood distribution calculating step of calculating, for each of the plurality of first images, a degree of similarity at each pixel position with respect to the object as a likelihood representing a likeness to the object, and calculating a first likelihood distribution indicating a distribution of likelihoods in the first image;

a trackability determining step of determining whether the object is trackable for each of the plurality of first images on the basis of the first likelihood distribution;

a second image acquiring step of acquiring a plurality of second images, wherein the second image acquiring step comprises:

in response to determining that the object is trackable for each of the plurality of first images, acquiring the plurality of second images which are transparent images of the patient generated at a time different from that of the plurality of first images and of which imaging directions are the same as those of the plurality of first images, and in response to determining that the object is trackable for one or more first images among the plurality of first images, acquiring the plurality of second images which are transparent images of the patient generated at a time different from that of the one or more first images and of which imaging directions are the same as those of the one or more first images, and not acquiring remaining one or more second images which are transparent images of the patient generated at a time different from that of the remaining one or more first images and of which imaging directions are the same as those of the remaining one or more first images;

a calculating step of calculating, for each of the plurality of second images, a degree of similarity at each pixel position with respect to the object as the likelihood representing a likeness to the object, and calculating a second likelihood distribution indicating a distribution of the likelihood in the second image;

a tracking step of determining a position of the object in the second image based on the second likelihood distribution, and tracking the position of the object; and a step of controlling irradiation with the radiation according to the position of the object.

8. A radiation therapy device irradiating a patient with a radiation while tracking a position of an object in the patient's body, the radiation therapy device comprising a processor configured to: acquire a plurality of first images which are transparent images of the patient and of which imaging directions are different; calculate, for each of the plurality of first images, a degree of similarity at each pixel position with respect to the object as a likelihood representing a likeness to the object, and calculate a first likelihood distribution indicating a distribution of likelihoods in the first image; determine whether the object is trackable for each of the plurality of first images on the basis of the first likelihood distribution; in response to determining that the object is trackable for each of the plurality of first images, acquire a plurality of second images which are transparent images of the patient generated at a time different from that of the plurality of first images and of which imaging directions are the same as those of the plurality of first images, and in response to determining that the object is trackable for one or more first images among the plurality of first images and that the object is not trackable for remaining one or more first images, acquire the plurality of second images which are transparent images of the patient generated at a time different from that of the one or more first images and of which imaging directions are the same as those of the one or more first images, and not acquiring remaining one or more second images which are transparent images of the patient generated at a time different from that of the remaining one or more first images and of which imaging directions are the same as those of the remaining one or more first images; calculate, for each of the plurality of second images, a degree of similarity at each pixel position with respect to the object as the likelihood representing a likeness to the object, and calculate a second likelihood distribution indicating a distribution of the likelihood in the second image;

determine a position of the object in the second image based on the second likelihood distribution, and track the position of the object; and control irradiation with the radiation according to the position of the object.

* * * * *